US00PP28511P2

(12) United States Plant Patent
Valin

(10) Patent No.: US PP28,511 P2
(45) Date of Patent: Oct. 10, 2017

(54) ***ISOTOMA* PLANT NAMED 'TMLU 1301'**

(50) Latin Name: *Isotoma axillaris*
Varietal Denomination: TMLU 1301

(71) Applicant: Branded Garden Products Ltd., Ipswich (GB)

(72) Inventor: Charles Valin, Harkstead (GB)

(73) Assignee: Branded Garden Products Ltd., Ipswich (GB)

( * ) Notice: Subject to any disclaimer, the term of this patent is extended or adjusted under 35 U.S.C. 154(b) by 30 days.

(21) Appl. No.: 14/999,014

(22) Filed: Mar. 17, 2016

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

*Primary Examiner* — Kent L Bell
(74) *Attorney, Agent, or Firm* — Barbara Campbell; James W. Weatherly; Cochran Freund & Young, LLC

(57) ABSTRACT

A new and distinct cultivar of *Isotoma* plant named 'TMLU 1301' that is characterized by short, compact self-branching growth habit, mid-green compound leaves and bright single flowers which are vibrant purple in color. Each flower of 'TMLU 1301' bears a central contrasting bright yellow-green eye.

1 Drawing Sheet

Genus and species: *Isotoma axillaris*.
Variety denomination: 'TMLU 1301'.

BACKGROUND OF THE NEW PLANT

The present invention relates to a new and distinct cultivar of *Isotoma*, which is grown as an ornamental annual bedding plant for use in the garden and landscape and in planted containers. The new cultivar is known botanically as *Isotoma axillaris*, and will be referred to hereinafter by the cultivar name 'TMLU 1301'. The genus *Isotoma* is occasionally known by the alternate name *Laurentia*.

During the 1990s, the inventor's employer had commenced in Ipswich, Essex, United Kingdom a seed breeding program in the genus *Isotoma* from which no cultivars were selected or introduced. In 2010, the inventor commenced a breeding program to develop named cultivars of *Isotoma* with the objectives of large flower size and novel flower colors. The inventor was able to utilize seeds and seedlings from the previous seed breeding program. The present invention is a result of the inventor's desire to develop a large flowered deep purple variety of *Isotoma*.

In 2010, the inventor carried out controlled pollination of the following seedlings. For the male parent, the inventor used a seedling raised as 'LU11022' (unreleased and unpatented) which exhibits very large deep pink flowers. For the female parent, the inventor used a seedling raised as 'LU11039' (unreleased and unpatented) which exhibited large violet-blue flowers. Within the offspring of this pollination, coded as 'LU12009', one plant in particular impressed the inventor for its naturally prolific basal and lateral branching and its very large glowing vibrant purple flowers. This plant was selected and was subsequently named 'TMLU 1301'.

'TMLU 1301' was first asexually propagated by the inventor in 2013 in Ipswich, Suffolk, United Kingdom. Asexual propagation was accomplished using tip cuttings. Since that time, under careful observation, the distinguishing characteristics of 'TMLU 1301' have been determined stable and uniform, and to reproduce true to type in successive generations of asexual propagation.

SUMMARY

The distinguishing characteristics of 'TMLU 1301' are as follows: In combination these traits set 'TMLU 1301' apart from all other existing varieties of *Isotoma* known to the inventor. 'TMLU 1301' has not been tested under all possible conditions and phenotypic differences may be observed with variations in environmental, climatic, and cultural conditions.

1. Plants of 'TMLU 1301' exhibit a short, compact growth habit.
2. Plants of 'TMLU 1301' are naturally self-branching and spreading. Pinching or pruning is not required to maintain a tidy plant.
3. The leaves of 'TMLU 1301' are deeply cut and are mid-green in color.
4. 'TMLU 1301' bears vibrant purple single flowers.
5. Each flower of 'TMLU 1301' bears a bright yellow-green eye which contrasts sharply with the purple color of the flower
6. 'TMLU 1301' flowers continually from early spring until fall. First flowering has been observed as early as March in California.
7. After one year of unrestricted growth, plants of 'TMLU 1301' are 30 cm in height and 30 cm in width.
8. 'TMLU 1301' prefers full sun in rich well-drained soil.
9. 'TMLU 1301' is a tender perennial which survives in USDA Zone 10 or warmer.

DESCRIPTION OF THE PHOTOGRAPHS

The photograph was taken of a six-months-old plant of 'TMLU 1301' which had been grown outdoors in a 10-cm container in Oxnard, Calif. The photograph illustrates the overall appearance of 'TMLU 1301' showing the colors of its foliage and flowers as true as it is reasonably possible to obtain in colored reproductions of this type.

DESCRIPTION OF THE NEW VARIETY

The following is a detailed botanical description of the new *Isotoma* cultivar named 'TMLU 1301'. Observations, measurements, values and comparisons were collected from a plant grown outdoors in Santa Barbara, Calif. The observed plant was approximately one-year-old and was growing in a 5-gallon container. The plant had been grown without the use of growth retardant chemicals or any pinching. Color determinations were made in accordance with The 2007 Royal Horticultural Society Colour Chart from London, England, except where general color terms of ordinary dictionary significance are used. The growing requirements of the new variety 'TMLU 1301' are similar to the species.

Botanical classification:

*Genus and species.*—*Isotoma axillaris.*

*Family.*—Campanulaceae.

Parentage: 'TMLU 1301' was selected as a seedling from the progeny of the following parents.

*Male parent.*—*Isotoma* seedling designated 'LU11022'.

*Female parent.*—*Isotoma* seedling designated 'LU11039'.

Plant:

*Habit and shape.*—Compact and upright.

*Commercial category.*—Annual.

*Use.*—As a bedding plant or container plant or for mixed combination plantings.

*Suggested commercial container size.*—9 cm container and larger.

*Propagation method.*—Vegetative cuttings.

*Rooting system.*—Fine.

*Vigor.*—Moderately vigorous once established.

*Crop time* (*average*).—3 months are required to produce a flowering plant in a 9 cm container from an unrooted cutting.

*Dimensions* (3 *months,* 9 *cm container*).—25 cm to 30 cm in height and spread.

*Dimensions* (*end of summer,* 10-*liter container*).—30 cm in height, 60 cm in spread.

*Cultural requirements.*—Performs best in full sun, with moderate water, and most soil types.

*Pest and disease susceptibility.*—None known to the inventor.

*Hardiness.*—Frost sensitive: survives over-winter in USDA Zone 10 and warmer.

*Special growing recommendations.*—None: plants are self-branching and naturally low-growing and spreading.

Stems:

*Branching habit.*—Both basal and lateral branching.

*Basal stem quantity.*—Approximately 10 basal stems produced in one season.

*Lateral stem quantity.*—Approximately 5 lateral stems per basal stem.

*Stem shape.*—Cylindrical.

*Surface.*—Glabrous.

*Stem color.*—138A.

*Stem length.*—15 cm to 20 cm.

*Stem diameter.*—4 mm at base.

*Stem strength.*—Moderately strong, wiry.

*Internode* (*average*).—1.5 cm.

Foliage:

*Leaf type.*—Pinnately compound.

*Leaf arrangement.*—Alternate.

*Leaf division.*—Simple.

*Leaf margin.*—Smooth, entire.

*Leaf surface* (*both surfaces*).—Glabrous.

*Leaf shape* (*outline*).—Narrowly elliptic.

*Leaf lobes.*—Typically three long lobes and 5 or 6 short lobes on each side.

*Leaf dimensions.*—7 cm to 9 cm in length, 3.0 cm to 4.5 cm in width.

*Lobe dimensions.*—Large lobes are 2 cm in length and up to 7 mm in width. Small lobes are 5 mm to 10 mm in length and up to 3 mm in width.

*Leaf color* (*adaxial surface*).—N137C.

*Leaf color* (*adaxial surface*).—138A.

*Leaf and lobe apex.*—Acute.

*Leaf base.*—Cuneate.

*Venation pattern.*—Pinnate.

*Vein color* (*both surfaces*).—As adjacent leaf tissue.

*Attachment.*—Petiolate.

*Petiole surface.*—Glabrous.

*Petiole color.*—138B.

*Petiole shape, dimensions.*—Caniculate, 1 cm length and 2.5 mm in width.

Inflorescence:

*Type.*—Solitary flower.

*Arrangement.*—Axillary.

*Blooming months.*—March to October.

*Flower quantity.*—Typically 2 open flowers and 4 to 6 buds on each lateral flowering branch.

*Flower aspect.*—Upright and outward facing.

*Flower type.*—Single, 5 petals fused at base to 5-lobed corolla tube.

*Flower dimensions.*—Diameter: 3.5 cm to 4.0 cm, depth (excluding corolla tube) 1 mm.

*Persistent or self-cleaning.*—Self-cleaning.

*Peduncle shape.*—Cylindrical.

*Peduncle surface.*—Glabrous.

*Peduncle color.*—138A except 144C at base.

*Peduncle dimensions* (*average*).—9 cm in length and 2 mm in diameter.

*Axillary peduncle angle.*—30° away from the vertical.

*Bud shape.*—Obovate.

*Bud apex.*—Acute.

*Bud color.*—145B.

*Rate of opening.*—Rapid, from 1 to 2 days from visible bud to fully open flower.

*Bud surface.*—Glabrous.

*Bud dimensions.*—8 mm in length, 4.5 mm in diameter.

*Corolla* (*tube*) *shape.*—Campanulate, 5-lobed.

*Corolla dimensions.*—Long tube, 2 cm in length and 3.5 mm. in diameter.

*Corolla surface* (*both surfaces*).—Glabrous.

*Corolla color* (*external surface*).—145B and 145C with light mauve longitudinal streaks closest to N80B.

*Lobes* (*petals*).—5 in number.

*Lobe arrangement.*—Rotate, two upper lobes slightly larger than three lower lobes. Palate or eye: Lower lobes cream-green at base giving appearance of strongly contrasting eye.

*Lobe shape.*—Obovate.

*Lobe dimensions* (*upper lobes*).—14 mm in length, 8 mm in width.

*Lobe dimensions* (*lower lobes*).—17 mm in height, 10 mm in width.

*Lobe* (*petal*) *arrangement*.—Apopetalous, very slightly overlapping, fused at base to fused corolla tube.

*Lobe color* (*adaxial surface*).—Ranges between N89C and N89D except base.

*Lobe base color* (*adaxial surface*).—The purple color N89C to N89D of the lobes stops abruptly laterally approximately 3 mm from lobe base, at which point lobe color becomes cream and green-yellow. NN155A and 1A are both present at the base of the lower lobes. Taken together, the lobe bases present the effect of a contrasting bright yellow-green eye in the purple-blue flower.

*Lobe color* (*abaxial surface*).—Very pale blue, paler than 91D.

*Lobe margin*.—Entire, edged N89C.

*Lobe surface* (*both surfaces*).—Glabrous.

*Lobe apex*.—Acuminate.

*Lobe base*.—Truncate (fused to corolla tube).

*Calyx shape*.—Campanulate.

*Calyx dimensions*.—5 mm in depth, 2 cm in diameter.

*Sepals*.—5 in number.

*Sepal shape*.—Very narrow lanceolate.

*Sepal dimensions*.—12 mm in length and 1 mm in width at sepal base.

*Sepals fused or unfused*.—Unfused.

*Sepal color* (*both surfaces*).—138A.

*Sepal margin*.—Entire.

*Sepal apex*.—Acute.

*Sepal base*.—Cuneate.

*Sepal surface* (*both surfaces*).—Glabrous.

Reproductive organs:

*Stamens*.—5 in number, attached approximately half-way along corolla tube.

*Stamen dimensions, color*.—12 mm in length, less than 1 mm in diameter, color between white and 144D.

*Anthers*.—Dorsifixed, oblong, 3 mm in length, 1 mm in width, color: N187C.

*Pollen amount*.—Moderate, color: 160B.

*Pistil*.—1 in number, length 2 cm, width 1.5 mm, color ranges between 145B and 145C.

*Stigma*.—Capitate, bi-lobed, 2 mm in diameter, color N186A.

*Ovary* (*undeveloped*).—Inferior, globose, 1 mm in diameter, color 151D.

Seeds: None observed.

COMPARISON TO PARENTAL LINES AND COMMERCIAL VARIETY

'TMLU 1301' may be compared with its parents. Whereas 'TMLU 1301' exhibits very large purple flowers, the male parent 'LU11022' exhibits very large deep pink flowers, and the female parent 'LU11039' exhibits large, but smaller, violet-blue flowers. In addition, neither of the parents exhibit the naturally vigorous branching that characterizes 'TMLU 1301'

The closest comparison plant to 'TMLU 1301' which is known to the inventor is *Isotoma axillaris* 'Beth's Blue' (unpatented). In comparison with 'Beth's Blue', 'TMLU 1301' bears much larger flowers with broader petals and a deeper and more vibrant purple color to the petals. In addition, plants of 'Beth's Blue' exhibit a more open growth habit.

I claim:

1. A new and distinct cultivar of *Isotoma* plant named 'TMLU 1301' as described and illustrated herein.

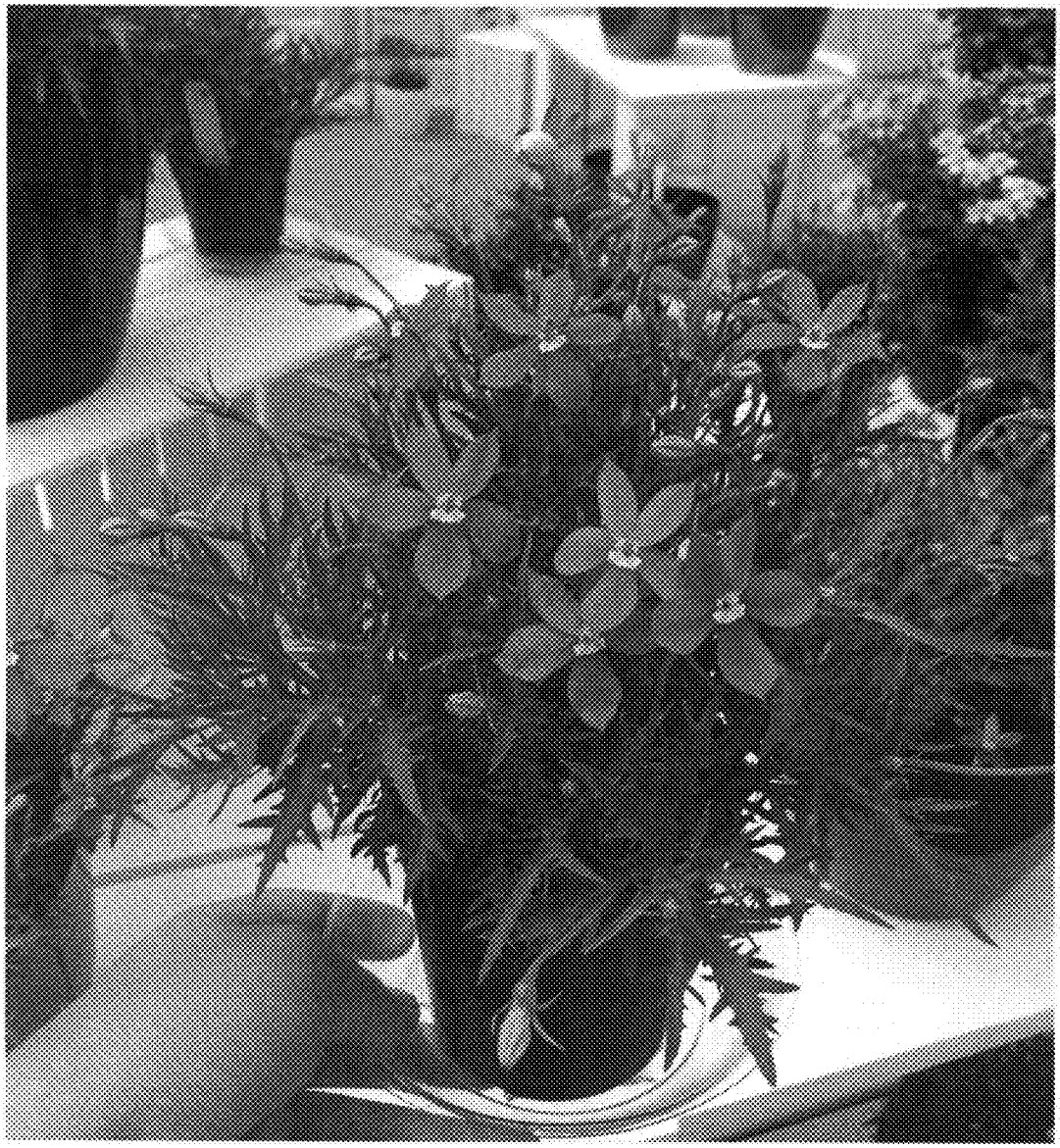

* * * * *